United States Patent [19]

Wakeman et al.

[11] 3,951,878

[45] Apr. 20, 1976

[54] IMIDAZOLINE OXIDES

[75] Inventors: Reginald L. Wakeman, Philadelphia, Pa.; Zdzislaw J. Dudzinski, Clifton; Arnold Lada, Montclair, both of N.J.

[73] Assignee: Millmaster Onyx Corporation, New York, N.Y.

[22] Filed: Nov. 23, 1971

[21] Appl. No.: 201,573

Related U.S. Application Data

[63] Continuation-in-part of Ser. No. 804,669, March 5, 1969, abandoned, which is a continuation-in-part of Ser. No. 562,522, July 5, 1966, abandoned.

[52] U.S. Cl. ............................... 252/542; 252/524; 252/529; 252/547; 260/309.6
[51] Int. Cl.² ......................................... C11D 3/26
[58] Field of Search ........... 252/542, 529, 547, 524, 252/106; 260/309.6

[56] References Cited
UNITED STATES PATENTS

| | | | |
|---|---|---|---|
| 3,098,794 | 7/1963 | Dohr et al. | 8/10.1 |
| 3,156,656 | 11/1964 | Libby | 252/542 |
| 3,202,714 | 8/1965 | Zimmerer et al. | 260/584 |
| 3,206,512 | 9/1965 | Koebner et al. | 260/583 X |
| 3,607,765 | 9/1971 | Wixon | 252/524 |

OTHER PUBLICATIONS
The Merck Index — 7th Edition — 1960, p. 1010.

*Primary Examiner*—Mayer Weinblatt
*Assistant Examiner*—Edith R. Buffalow
*Attorney, Agent, or Firm*—Arthur A. Jacobs

[57] ABSTRACT

A surface-active composition consisting essentially of (a) a compound having the structure:

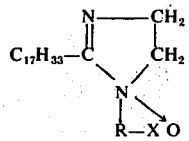

wherein R is a member of the group consisting of $C_2H_4$ and $C_3H_6$ and X is a member of the group consisting of OH and $NH_2$, and (b) another surface-active agent selected from the group consisting of anionic, cationic and non-ionic surface active agents.

4 Claims, No Drawings

IMIDAZOLINE OXIDES

This is a continuation-in-part of co-pending application Ser. No. 804,669, filed Mar. 5, 1969, which is, in turn a continuation-in-part of co-pending application Ser. No. 562,522, filed July 5, 1966 both now abandoned.

This invention relates to amine oxides having surfaceactive and other desirable properties, and it more particularly relates to alkenyl imidazoline oxides.

In accordance with the present invention, highly effective detergent, cosmetic and other compositions are formed with the inclusion of oxides of heptadecenyl-2-imidazolines having the structural formula:

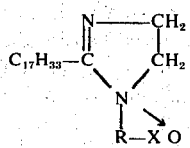

wherein R may be either $C_2H_4$ or $C_3H_6$ and X may be either OH or $NH_2$, and wherein the arrow indicates a semi-polar bond.

These 2-imidazolines may be prepared by condensing oleic acid (9-octadecenoic acid), or its commercial equivalent known as "red oil", with diethylene triamine ($NH_2C_2H_4NHC_2H_4NH_2$) or aminoethyl ethanolamine ($NH_2CH_2CH_2NHCH_2CH_2OH$) by standard procedures, whereby two molecules of water are eliminated. Such techniques include azeotropic distillation with a suitable solvent, or heating under reduced pressure or in a stream of inert gas. Thereafter, unreacted amine may be stripped off from the reaction mass, leaving a product which consists essentially of a heptadecenyl-2imidazoline having either an aminoethyl or a hydroxyethyl substituent on the 1-nitrogen atom.

The imidazolines thus obtained may then be oxidized by treatment with a suitable oxidizing agent, such as hydrogen peroxide, an organic peroxide, or ozone, to produce the desired heptadecenyl imidazoline oxides. Oxidation processes of this type are well-known in the art. In general it is preferred to use hydrogen peroxide.

The following examples are illustrative of the procedures involved, but are not intended to limit the invention except as claimed.

EXAMPLE I

A glass-lined kettle fitted with an agitator, a condenser, phase separator and solvent return, a receiver, and a source of vacuum, was charged with 280 pounds (or one mol) of high grade oleic acid (Groco 6), 125 pounds (or 1.2 mol) of aminoethyl ethanolamine, and 33 pounds of toluene. The kettle and its auxiliaries were purged with nitrogen, and the mixture was heated while being agitated. At about 125°C., distillation began, at which time the nitrogen was cut off from the pot and switched to the vent of the condenser. Water and toluene distilled azeotropically, and the toluene was returned to the reactor. The reaction proceeded for about 2 to 3 hours, during which hours the temperature rose to about 175°–195°C.

At this point a partial vacuum was applied, and both water and toluene were stripped off the charge. When distillation appeared complete, the receiver was disconnected from the apparatus, and full vacuum was applied gradually, to about 5–10 mm. pressure, and to a pot temperature of 200°C., to remove excess aminoethylethanolamine. The product, after cooling under vacuum, was a light reddish-amber viscous fluid with a yield of 350 pounds, and consisted essentially of 1-ethoxy-2-heptadecenyl-2-imidazoline.

EXAMPLE II

In the equipment of Example I, a dephlegmator was introduced into the still-head and this in turn was connected to a totaltake off condenser and receiver.

The charge consisted of 280 pounds of oleic acid (or 1 mol), and 340 pounds (or 3.3 mol) of diethylene triamine. The system was purged with nitrogen, and the charge was then heated to 150°C. A partial vacuum was drawn until active distillation began; the dephlegmator was cooled to a temperature intermediate between that of the boiling points of diethylene triamine and water at ambient pressure. A distillate, rich in water, was stripped off into the receiver, while a fraction rich in diethylene triamine was returned to the reactor. When the vapor temperature indicated a negligible proportion of water, the receiver was charged and the dephlegmator cut out. The excess diethylene triamine was then removed at up to full vacuum and at 150°C. The batch was then cooled and removed. The yield was about 350 pounds, and consisted of at least 85% of 1-aminoethyl-2-heptadecenyl-2-imidazoline, with a small proportion of 1-oleylamidoethyl-2-heptadecenyl-2-imidazoline as a by-product.

The excess diethylene triamine is easily recovered for re-use. By the introduction of a suitable factionating column into the reaction system, it is possible to remove the water essentially completely from the amine, and with negligible loss of amine, during the course of the reaction.

EXAMPLE III

A sample of 1-ethoxy-2-heptadecenyl-2-imidazoline prepared as in Example I was titrated and found to have an equivalent weight of 370 (theory=350.5).

One mol of this was charged, along with 120 grams of isopropanol 99 and 60 grams of distilled water, into a 2 liter round-bottom flask fitted with an agitator, a reflux condenser, a dropping funnel and an immersion bath for cooling and heating.

The dropping funnel was charged with 105 grams (or 1.05 mols) of 34% hydrogen peroxide. The charge was maintained at 37°C. during the gradual addition of the peroxide over a period of 45 minutes. The reaction is exothermic and, on completion of the addition, the temperature falls. Agitation was continued for a short time longer to insure completion of the oxidation. The product was a clear amber solution. 640 grams of distilled water was then added with continued agitation, to yield a 28% active viscous solution of very light color. Only traces of free hydrogen peroxide remained. Conversion to 1-ethoxy-2-heptadecenyl-2-imidazoline oxide, by differential titration, was of the order of 95%. The pH of the solution was about 8.

A still lighter product can be obtained by using only 95 mol per cent of hydrogen peroxide.

While a product of excellent color is obtained at about 37°C., it is not necessary to restrict it. Any temperature from 25°C. to 100°C. may be used; however, the product darkens as the temperature rises, and temperature control by cooling becomes increasingly difficult at low temperatures.

Instead of isopropanol, other polar solvents such as ethanol, methanol or the like may be substituted. The alcohol serves as a diluent to facilitate heat transfer, and to keep the viscosity within workable range.

It is not essential to add water during the reaction. On the other hand, the reaction may be conducted in water alone although this involves generally undesirable foaming and an indefinite induction period.

The concentrate, before dilution to about 28% strength, is about 70% active, and may be employed as such if desired.

Generally, oxidation occurs at the 1-nitrogen. However, by employing a larger excess of hydrogen peroxide, some further oxidation takes place, as evidenced by the fact that while decomposition of added hydrogen peroxide is insignificant, the amount of unreacted residual peroxide is small. The additional oxidation is believed to occur at the 3-nitrogen.

EXAMPLE IV

The 1-aminoethyl-2-heptadecenyl-2-imidazoline of Example II was processed in the same manner as used in Example III.

The sample used as the starting material assayed about 85% imidazoline, the remainder being mainly amidoimidazoline.

The oxidation proceeded in the same way, to yield 1-aminoethyl-2-heptadecenyl-2-imidazoline oxide.

The above examples illustrate the preparation of the compounds where R is $C_2H_4$. However, the same procedures may be used where R is $C_3H_6$, but merely substituting isopropylene-containing starting materials, such as diisopropylene triamine, etc., for the ethylene-containing compounds.

The aforesaid imidazoline oxides are useful surface-active agents. As such they may be employed as components of such detergents, cosmetic and other formulations as dishwashing compounds, shampoos, light- and heavy-duty detergent compositions, and the like. Since they are non-ionic in character at and above the neutral point, they are compatible with anion-active, cation-active and non-ionic agents. They also impart disinfecting or sanitizing properties, since they are bactericidal and fungicidal.

Anionic synthetic surface-active agents (surfactants) are generally described as those compounds which contain both hydrophilic and lyophilic groups in their molecular structure and ionize in an aqueous medium to give anions containing both the lyophilic group and hydrophilic group, but especially the latter. The class of surfactants particularly useful in the practice of this invention are those classified as detersive surfactants.

Illustrative of the preferred anionic surfactants used to practice this invention are the alkyl aryl sulfonates, the alkyl sulfates and mixtures thereof.

Compounds illustrative of the alkyl aryl sulfonates useful in the practice of this invention include monohexanolammonium dodecylbenzene sulfonate; triisopropanolammonium tricosyl benzene sulfonate; diisobutanolammonium dodecylbenzene sulfonate; 1-n-decanolammonium octyl benzene sulfonate, triethanolammonium nonylbenzene sulfonate; triisopropanolammonium dodecylnaphthalene sulfonate; monoethanolammonium heptadecylbenzene sulfonate; ammonium eicosyl naphthalene sulfonate; ethanolammonium undecylnaphthalene sulfonate; triethanolammonium dodecyl benzene sulfonate; ethanolammonium tetradecyl benzene sulfonate; ammonium octadecyl benzene sulfonate; triisopropanolammonium decylbenzene sulfonate; ammonium pentadecyl benzene sulfonate as well as the corresponding alkali metal (i.e. sodium and potassium) salts of these and other sulfonates. The preferred alkyl sulfates useful in the practice of this invention are those represented by the general formula:

$$RSO_3M$$

where M is either an alkali metal, such as sodium or potassium, or ammonium, or an alkanol substituted ammonium radical represented by the following formula:

$$NH_nR_m$$

where $n$ is an integer from 1 to 4, $m$ is an integer from 0 to 3 and $m+n$ equals 4, and R is an alkanol radical.

Compounds illustrative of the above alkyl sulfate class include triisopropanolammonium tetracosyl sulfate; 2-hexanolammonium hexadecyl sulfate; 1-decanolammonium 2,7,8-trimethyldecyl sulfate; monoethanol ammonium nonyl sulfate; ammonium decyl sulfate; ammonium 2,3,5-trimethylhexyl sulfate; triethanolammonium octyl sulfate; n-dipentanolammonium octadecyl sulfate; 3-heptanolammonium nonyl sulfate, as well as the corresponding alkali metal (i.e. sodium and potassium) salts of these and other sulfates.

Although the preferred anionic detersive surfactants in the practice of this invention are the alkyl aryl sulfonates and the alkyl sulfates, other anionic detersive surfactants which are water soluble and/or mono and dihydroxyl alcohol soluble can also be used. For example, those sulfated oxyethylated phenols of the following general formula can be used:

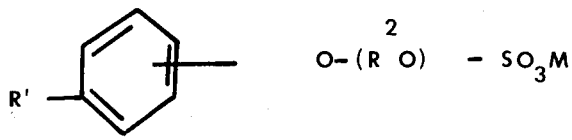

where R' is a straight or branched chain alkyl group having from about 5 to about 24 carbon atoms, $R^2$ is an alkyl radical containing from 2 to 4 carbon atoms, $x$ is an integer from 3 to 30 and M is either an alkali metal, ammonium or an alkanol substituted ammonium radical containing from 1 to 10 carbon atoms represented by the following general formula:

$$NH_nR_m$$

where $n$ is an integer of from 1 to 4 and $m$ is an integer of from 0 to 3 and $n+m$ equals 4 and R is an alkanol radical.

Compounds illustrative of the sulfated oxyethylated alkyl phenol class of anionic surface active agents useful in the practice of this invention include ammonium nonylphenoxy tricosapropyleneoxy sulfate; triisopropanolammonium dodecylphenoxy hexadecaethyleneoxy sulfate; ammonium decylphenoxy tripropyleneoxy sulfate; monoethanolammonium octylphenoxy decabutyleneoxy sulfate; as well as 1-monodecanolammonium hexylphenoxy tridecaethyleneoxy sulfate; triethanolammonium dodecylphenoxy eicosylpropyleneoxy sulfate; dibutanolammonium decylphenoxy cosabutyleneoxy sulfate; monoethanolammonium octylphenoxy hexaethyleneoxy sulfate; diethanolammonium tridecylphenoxy tetradecapropyleneoxy sulfate; monobutanolammonium tetradecylphenoxy heptapropyleneoxy sulfate; triethanolammonium cosylphenoxy oxtadecaethyleneoxy sulfate; and ethanolammonium dodecylphenoxy tridecabutyleneoxy sulfate, as well as the corresponding alkali metal salts of these and other similar sulfates.

Preferred sulfated oxyethylated alkylphenols include triethanolammonium dodecylphenoxy decaethyleneoxy sulfate; monoethanolammonium tetradecylphenoxy decapropyleneoxy sulfate; monoethanolammonium octylphenoxy pentaethyleneoxy sulfate; diisopropanolammonium octadecylphenoxy decaethyleneoxy sulfate; ammonium pentaeicosaethyleneoxy sulfate; monoethanolammonium tridecylphenoxy tridecaethyleneoxy sulfate; triethanolammonium tetradecylphenoxy decaethyleneoxy sulfate; triisopropanolammonium dodecylphenoxy octadecaethyleneoxy sulfate and the corresponding alkali metal compounds.

Other anionic detersive surfactants which can be used include the alkali metal, ammonium and alkanol substituted ammonium salts containing at most 10 carbon atoms of alkyl containing sulfosuccinic acid such diamyl, dihexyl, dioctyl esters of sulfosuccinic acid. In addition, a number are described in Schwartz, Perry and Berch, Surfact Active Agents and Detergents, Vol. II, Interscience Publishers, New York (1958).

The cation-active or cationic surface active agents are characterized by the fact that the hydrophobic group forms part of a cation when the compound is dissolved in water. The class may be regarded as consisting broadly of those bases which contain a typical hydrophobic group, and may be sub-classified according to the essential nature of the functional basic group. The amines and quaternary ammonium salts constitute by far the largest group of cationic surface active agents. Aside from the amines and quaternary ammonium compounds there is a group of nitrogeneous bases including guanidines, hydrazines, amine oxides, basic nitrogen heterocyclic substances, etc., around which surface active agents have been synthesized. Finally, there is the group of nonnitrogenous bases, of which the most noteworthy are the sulfonium compounds.

The cationic surfactants utilizable in this invention are of the type generally described in Schwartz, Perry and Berch, "Surface Active Agents and Detergents", Vol. II, pp. 103-119, Interscience Publishers, Inc., New York (1958).

Non-ionic surfactants can be broadly described as compounds which do not ionize but acquire hydrophilic characteristics from an oxygenated side chain such as polyoxyethylene. The lyophilic part of the non-ionic surfactant molecule may come from fatty acids, phenol, alcohols, amides or amines. The non-ionic detersive surfactants are usually made by reacting an alkylene oxide such as ethylene oxide, butylene oxide, propylene oxide and the like with fatty acids, a straight or branched chain alcohol, phenols, thiophenols, amides and amines to form polyoxyalkylene glycol ethers and esters, polyoxyalkylene alkyl phenols and polyoxyalkylene thiophenols, and polyoxyalkylene amides and the like. It is generally preferred to react from about 3 to about 30 moles of alkylene oxide per mole of the fatty acids, alcohols, phenols, thiophenols, amides or amines.

Illustrative of these non-ionic detersive surfactants are the products obtained from the reaction of alkylene oxide such as ethylene oxide and/or propylene oxide, with an aliphatic alcohol having from 8 to 18 carbon atoms, such as octyl, nonyl, decyl, octadecyl, dodecyl, tetradecyl and the like; with an alkyl phenol in which the alkyl group contains between 4 and 20 carbon atoms, such as butyl, dibutyl, amyl octyl, dodecyl, tetradecyl and the like; with an alkyl amine in which the alkyl group contains between 1 to 8 carbon atoms; and with a fatty alkanol amide in which the alkyl group contains between 6 and 24 carbon atoms. Also the sugar esters, the mannitol esters and the sorbital esters. Phosphonium compounds may also be used.

Compounds illustrative of synthetic non-ionic surface-active agents include the products obtained from condensing from 3 to 30 moles of ethylene oxide or propylene oxide per mole of the following: propylene glycol, ethylene diamine, diethylene glycol, dodecyl phenol, nonyl phenol, tetradecyl alcohol, N-octadecyl diethanolamide and N-dodecyl monoethanolamide. A number of non-ionic detersive surfactants are described in Schwartz, Perry and Berch, Surface Active Agents and Detergents, Vol. II, Interscience Publishers, New York (1958).

Builders and other additives such as corrosion inhibitors, perfumes, dyes, brightening agents, antiredeposition agents, etc., may also be included in the composition without affecting its primary purpose. An example of a builder which may be used is a finely divided sodium polyphosphate selected from the group consisting of sodium tripolyphosphate, tetrasodium pyrophosphate and mixtures thereof.

It is possible in a liquid detergent of this invention to incorporate an inorganic nonphosphate salt such as sodium sulfate. Additives, such as sodium carboxymethyl cellulose as an anti-redeposition agent, or anhydrous sodium silicate as corrosion inhibitor; and perfumes, dyes, and brightening agents may also be added. The antiredeposition agents, corrosion inhibitors, perfumes, dyes, and brightening agents, if used, are generally added in amounts of below about 10% by weight.

Illustrative of the use of the instant compounds in detergent compositions and the like are the following examples:

EXAMPLE V

A liquid dishwashing compound was prepared according to the following formula:

| Components | Parts by Wt. |
|---|---|
| The 1-ethoxy-2-heptadecenyl-2-imidazoline oxide of Example III (28% concentration) | 10 |
| Triethanol amine "Lorol 5" sulfate (40% concentration) ("Lorol 5" is a DuPont mixture of fatty alcohols) | 10 |
| Sodium dodecyl benzene sulfonate (60% concentration) | 10 |
| Ethyl alcohol | 10 |
| Water | 60 |

The above components were thoroughly mixed at room temperature to form the liquid composition.

A similar composition may be prepared in the same manner, substituting the 1-aminoethyl-2-heptadecenyl- 2-imidazoline oxide of Example IV for the imidazoline oxide of Example III. A similar compound may also be made by the same procedure but substituting the aforesaid isopropylene-containing compounds for the ethylenecontaining imidazoline oxides.

EXAMPLE VI

A heavy duty general purpose detergent was prepared by mixing in a sigma type tumble mixer, the following components:

| Components | Parts by Wt. |
| --- | --- |
| Sodium tripolyphosphate | 45 |
| Sodium sulfate | 25 |
| Sodium metasilicate | 5 |
| Sodium "Lorol 5" sulfate (90% concentration) | 5 |
| Sodium dodecyl benzene sulfonate (60% concentration) | 20 |
| The 1-aminoethyl-2-heptadecenyl-2-imidazoline oxide of Example IV (28% concentration) | 10 |

The electrolytes were tumbled, while being heated to about 80°C., or until most of the water was driven off, and the surface-active components were added gradually. As the water was driven off during the tumbling, a free-flowing powder remained.

The same procedure can be used to obtain a similar product but substituting the 1-ethoxy-2-heptadecenyl-2-imidazoline oxide of Example III. The same procedure can also be used while substituting the isopropylene-containing imidazoline oxides.

EXAMPLE VII

A liquid shampoo was prepared using the following components:

| Components | Parts by Wt. |
| --- | --- |
| Triethanolamine "Lorol 5" sulfate (40% concentration) | 30 |
| Triethanolamine laurate | 5 |
| The 1-ethoxy-2-heptadecenyl-2-imidazoline oxide of Example III (28% concentration) | 10 |
| Hexylene glycol | 10 |
| Water | 45 |

These components were mixed at room temperature to form the liquid shampoo.

Here again, the imidazoline oxide of Example IV may be substituted for that of Example III or the corresponding isopropylene imidazoline oxides may be used instead of the ethylene-containing compounds.

EXAMPLE VIII

A shampoo was prepared by mixing at room temperature, the following composition:

| Components | Parts by Wt. |
| --- | --- |
| Millmaster-Onyx "Maprofix ES" 30% (a sodium "lorol" ether sulfate) | 40 |
| Amine oxide of Example (III or IV) | 10 |
| NaCl | 0.1 - 0.2 |
| Ethylene glycol | 2 |
| Perfume | 0.5 |
| Water | 47.3 |

EXAMPLE IX

A liquid dishwashing compound was prepared by mixing at room temperature, the following components:

| Components | Parts by Wt. |
| --- | --- |
| Millmaster-Onyx "Neutronyx S 60" (the ammonium salt of a sulfated alkylphenol polyglycol ether) 60% active | 30 |
| The amineoxide of Example III | 10 |
| Sodium xylene sulfonate, 40% | 5 |
| Water | 55 |

EXAMPLE X

A bar soap was prepared using a 4:1 ratio of high-grade tallow coconut oil saponified with caustic soda by a standard commercial process. It was finished at about 65% strength as fatty acid, and at low free alkali and salt content. The following mixture was milled, compressed, extruded and formed into bars of soap:

| Components | Parts by Wt. |
| --- | --- |
| Coconut-tallow soap | 65 |
| General Aniline & Film Corp. "Igepon AC 78", a coconut-oil acid ester of sodium isethionate | 25 |
| The amine oxide of Example III | 10 |

Perfume and color may be added if desired.

EXAMPLE XI

A heavy duty laundry detergent was prepared by mixing at room temperature the following components:

| Components | Parts by Wt. |
| --- | --- |
| Alkyl benzene sulfonate, 60% active | 20 |
| The amine oxide of Example III (or IV) | 11 |
| General Aniline and Film Corp.'s "GAFAC LO", a sodium salt of a complex organic phosphate ester, 88% active | 5 |
| Sodium tri-poly phosphate | 10 |
| Sodium xylene sulfonate, 40% active | 10 |
| Water | 44 |

Color and perfume are optional additives.

EXAMPLE XII

| Components | Parts by Wt. |
| --- | --- |
| Alkylphenol polyglycol ether (9.5 E.O.) | 10 |
| Amine oxide of Example III (or IV) | 15 |
| Hexylene glycol | 3 |
| Water (odor and color optional) | 72 |

This mixture, prepared at ambient conditions, is a nonionic dishwashing compound.

EXAMPLE XIII

A non-ionic liquid hand soap was prepared by mixing at room temperature:

| Components | Parts by Wt. |
| --- | --- |
| Alkylphenol polyglycol ether (11 mols E.O.) | 5 |

-continued

| Components | Parts by Wt. |
|---|---|
| Amine oxide of Example III (or IV) | 30 |
| Propylene glycol | 2 |
| Water | 63 |

EXAMPLE XIV

A "waterless" hand cleaner was prepared in two parts, separately; then mixed:

| Part A | |
|---|---|
| Components | Parts by Wt. |
| Potash-rosin soap, 40% active | 30 |
| The amine oxide of Example III (or IV) | 20 |
| Water | 15 |
| Part B | |
| Deodorized kerosene | 30 |
| Polyethylene glycol 600 soybean fatty-acid ester | 5 |

Part B was added gradually to part A with constant agitation at room temperature. The product was a clear viscous paste.

EXAMPLE XV

A detergent-sanitizer was prepared by mixing at room temperature the following components:

| Components | Parts by Wt. |
|---|---|
| Millmaster-Onyx "BTC 2125" (a mixture of alkyl dimethyl benzyl and alkyl dimethyl ethylbenzyl ammonium chlorides, 50:50, and 50% active) | 6 |
| Alkylphenol polyglycol ether (11 E.O.) | 4 |
| Soda Ash | 2 |
| Sodium tripolyphosphate | 3 |
| The amine oxide of Example III (or IV) | 5 |
| Water | 80 |

Instead of "BTC 2125" an equivalent amount of lauryl dimethyl dichlorobenzyl ammonium chloride, dodecyl trimethyl ammonium chloride or dodecylbenzyl trimethyl ammonium chloride may be substituted.

The invention claimed is:

1. A surface-active composition consisting essentially of (a) a surface-actively effective amount of a compound having the structure:

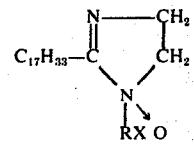

wherein R is a member of the group consisting of $C_2H_4$ and $C_3H_6$ and X is a member of the group consisting of OH and $NH_2$, and (b) a surface-actively effective amount of another surface-active agent selected from the group consisting of anionic, cationic and non-ionic surface-active agents.

2. The composition of claim 1 wherein the proportion of (a) to (b) is from about 1:9 to about 6:1 by weight of the composition.

3. A method of cleaning and sanitizing an object which comprises applying to said object a composition consisting essentially of (a) a surface-actively effective amount of a compound having the structure:

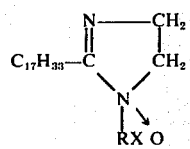

wherein R is a member of the group consisting of $C_2H_4$ and $C_3H_6$ and X is a member of the group consisting of OH and $NH_2$, and (b) a surface-actively effective amount of another surface-active agent selected from the group consisting of anionic, cationic and non-ionic surface-active agents.

4. The method of claim 3 wherein said other surface-actively agent is present in a proportion of (a) to (b) of about 1:9 to about 6:1 by weight of the composition.

* * * * *